United States Patent [19]
Willer et al.

[11] Patent Number: 5,162,494
[45] Date of Patent: Nov. 10, 1992

[54] ISOTACTIC POLY(GLYDICYL NITRATE) AND SYNTHESIS THEREOF

[75] Inventors: Rodney L. Willer, Newark, Del.; Alfred G. Stern, Elkton, Md.; Robert S. Day, Newark, Del.

[73] Assignee: Thiokol Corporation, Ogden, Utah

[21] Appl. No.: 609,198

[22] Filed: Nov. 5, 1990

[51] Int. Cl.⁵ .................. C08G 65/10; C08G 65/18; C08G 65/20
[52] U.S. Cl. .......................... 528/408; 528/409; 528/417; 528/421
[58] Field of Search .................. 528/408, 409, 417

[56] References Cited

U.S. PATENT DOCUMENTS

| | | | |
|---|---|---|---|
| 3,305,565 | 2/1967 | Mueller | 260/348.6 |
| 3,531,534 | 9/1970 | Adolph | 260/614 |
| 3,557,181 | 7/1971 | Lakritz et al. | 260/453 |
| 4,393,199 | 7/1983 | Manser | 528/408 |
| 4,511,742 | 4/1985 | Yu | 568/621 |

OTHER PUBLICATIONS

S. D. Morse, Polymerization and Modifications of Low Molecular Weight Polyethers, U. of Dayton Research Inst., Report No. UDR-TR-83-116, 40 pages, Oct. 1983.
R. Willer et al., Proceedings of the Jt. Int'l Symp. on Comp. of Plastics and other Mat'ls with Expl., Prop., Pyrotech and Processing of Expl. Prop. and Ingredients, Oct. 23-25 1989, Virginia Beach, VA, pp. 258-269.
E. Colclough et al., Proceedings of the Jt. Int'l Symp. on Comp. of Plastics and other Mat'ls with Expl., Prop., Pyrotech and Processing of Expl., Prop. and Ingredients, Oct. 23-25 1989, Virginia Beach, VA, pp. 235-240.
D. Debenham, Proceedings of the Jt. Int'l Symp. on Comp. of Plastics and other Mat'ls with Expl., Prop., Pyrotech and Processing of Expl., Prop. and Ingredients, Oct. 23-25 1989, Virginia Beach, VA pp. 119-129.
S. Penczek et al., Lecture at IUPAC 6th Int'l Symp. on Cationic Polymerization & Related Processes Ghent, Aug. 1983, "Cationic Polymerization and Related Processes", E. J. Goethals Ed., Academic Press, 1984, pp. 139-154.
K. Brzezinska et al., Makromol. Chem., Rapid Commun., 7, pp. 1-4, (1986).
S. Penczek et al., Makromol. Chem. Macromol. Symp., 3, pp. 203-217 (1986).
M. Bednarek et al., Makromol. Chem. Suppl., 15, pp. 49-60 (1989).
C. C. Gonzales et al., Makromol. Chem., 190, pp. 1217-1224 (1989).
Naval Ordnance Laboratory NAVWEPS Report 7409, A Survey of Nitro-Organic Compounds Related to Solid Propellant Systems (U), pp. 34-37, 61-64, 121, 129, 130, 132, 134, 137, 138, 143-146, Jun. 20, 1961.
U.S. Naval Ordnance, NAVORD Report 2028, Polyglycidyl Nitrate, Part 1, Preparation and Characterization of Glycidyl Nitrate, NOTS 685, 13 pages plus abstract, May 6, 1953.
U.S. Naval Ordnance NAVORD Report 2028, Polyglycidyl Nitrate, Part 2, Preparation and Characterization of Polyglycidyl Nitrate, NOTS 686, 20 pages plus abstract, May 7, 1953.
Jet Propulsion Laboratory, Publication No. 93 High-Performance Polyglycidyl Nitrate-Polyurethane Propellants, 33 pages, Mar. 29, 1957.
Defense Technical Information Center (DTIC), Document No. AD 144756, 1957.
Defense Technical Information Center (DTIC), Document No. AD 139462, 1957.
ACS Symp. Series 286, Ring-Opening Polymerization Kinetics, Mechanism and Synthesis, Chapter 25, Cationic Ring-Opening Polymerization of Epichlorohydrin in the Presence of Ethylene Glycol, Y. Ohamoto, pp. 361-372, J. E. McGrath, editor, ACS 1985.
ACS Symp. Series 286, Ring-Opening Polymerization Kinetics, Mechanism and Synthesis, Chapter 20, Homopolymerization of Epoxides in the Presence of Fluorinated Carbon Acids, J. Robins et al, pp. 263-274, J. E. McGrath, editor, ACS 1985.
Translation of article by Y. I. Estrin et al. Vysokomol, soyed., A10: No. 11, Kinetics of Polymerization of Epichlorohydrin Glycidyl Nitrate Catalyzed by $BF_3$, pp. 2589-2599, 1968.
Translation of article by A. I. Kuzayev et al, Vysokomol, soyed., A11: No. 5, Polymerization Kinetics of Tetrahydrofuran Caused by $BF_3$.THF in the Presence of Glycidyl Nitrate in 1,2-Dichloroethane, pp. 989-994, 1969.
Translation of article by S. G. Entelis et al, Vysokomol, soyed., A13: No. 6, Pegularities of Cationic Polymerization of Cyclic Ethers, pp. 1438-1446, 1971.
G. V. Korovina et al., J. Poly. Science: Part C, No. 16 pp. 3575-3579 (1968).
J. M. Klunder et al., J. Org. Chem. 51, 3710-3712, 1986.
J. M. Klunder et al., J. Org. Chem. 54, 1295-1304, 1989.
K. E. Stellar, A.C.S. Symp. Series, Polyethers, Chapter 9, Irregular Structures in Polyepichlorohydrin, 136-149, 1975.

*Primary Examiner*—John Kight, III
*Assistant Examiner*—Shelley A. Wright
*Attorney, Agent, or Firm*—Cushman, Darby & Cushman

[57] ABSTRACT

Isotactic poly(glycidyl nitrate) useful in solid propellants is produced by polymerizing chiral (R) glycidyl nitrate or its enantiomer, (S) glycidyl nitrate. Chiral (R) glycidyl nitrate or its enantiomer is prepared by sequential treatment of chiral (S) glycidyl tosylate or its enantiomer with nitric acid and sodium hydroxide. Chiral (S) glycidyl tosylate or its enantiomer, (R) glycidyl tosylate, can be produced by Sharpless epoxidation of allyl alcohol or by direct tosylation of commercially available chiral glycidol. Likewise, chiral (R) glycidyl nitrate or its enantiomer, (S) glycidyl nitrate, can be prepared direcly via nitration of (S) or (R) glycidol, respectively.

8 Claims, No Drawings

ISOTACTIC POLY(GLYDICYL NITRATE) AND SYNTHESIS THEREOF

FIELD OF THE INVENTION

This invention relates to isotactic poly(glycidyl nitrate) useful in solid propellants and the preparation thereof from chiral 2-(R)-glycidyl nitrate or its enantiomer, 2-(S)-glycidyl nitrate.

BACKGROUND OF THE INVENTION

Solid high-energy compositions, such as propellants, explosives, gasifiers, or the like, comprise solid particulates, such as fuel particulates and/or oxidizer particulates, dispersed and immobilized throughout a binder matrix comprising an elastomeric polymer.

Binders previously used in composite solid propellant formulations have generally been non-energetic polymers such as polycaprolactones, polyethyleneglycols or polybutadienes. Since about 1950 there has been a considerable need to develop energetic binders with satisfactory mechanical properties in order to provide safer binders at higher energy levels and to increase the energy level or specific impulse in a propellant formulation. For the most part only nitrocellulose has found usefulness as an energetic polymer binder. However, nitrocellulose suffers from undesirable mechanical properties. Alternatively, it has been proposed to employ conventional non-energetic polymer binders in combination with energetic plasticizers such as for example, nitroglycerine, butanetriol trinitrate, and trimethylolethane trinitrate. It has also been suggested that the energetic polymer nitrocellulose be employed with either non-energetic or energetic plasticizers in an attempt to improve mechanical properties. However, none of these proposals has led to fully acceptable energetic binder formulations.

Thus, there has been a continuing need for energetic polymers to be available for use in formulating solid high-energy compositions, such as propellants, explosives, gasifiers and the like. In this regard much recent work has centered on attempts to produce acceptable energetic polymers of glycidyl azide polymer and poly(oxytanes). A problem with elastomeric binders formed from poly(oxytanes) is their tendency to have mechanical characteristics less than that which would be desirable for a high-energy composition, particularly for a rocket motor propellant. It is especially difficult to provide poly(oxytane) binders having adequate stress capabilities. On the other hand glycidyl azide polymer is synthesized by first polymerizing epichlorohydrin to poly(epichlorohydrin) which is then converted to glycidyl azide polymer by reaction with sodium azide in dimethylsulfoxide. Beside the lack of a simple synthesis process, the production of glycidyl azide polymer requires relatively expensive reagents. Moreover, even after the polymer is synthesized it has been found that unplasticized glycidyl azide polymer-ammonium perchlorate solid propellants require about 78% solids to optimize Isp at about 254 sec.

Since the early 1950's poly(glycidyl nitrate), hereinafter referred to as PGN, has been known and recognized as a possible energetic prepolymer. The initial work on PGN was done by Thelan et al. at the Naval Ordnance Test Station (NOTS, now NWC). They studied the polymerization of racemic glycidyl nitrate by a variety of Lewis acid catalysts with most of the work centering on the use of stannic chloride as a catalyst. No propellants were prepared by the NOTS workers and they noted that one drawback to their synthesis was the laborious purification procedure.

Atactic PGN AND PGN propellants were next examined at the Jet Propulsion Laboratory (JPL) by Ingham and Nichols and at Aerojet General Corporation by Shookhoff and Klotz. The JPL workers found that PGN made using boron trifluoride etherate was low in both functionality (i.e. <2) and molecular weight (MW=1500) and therefore polyurethane propellants made from this PGN had poor mechanical properties. Similar observations were made by the Aerojet workers. In summary, it has long been recognized that PGN may be an excellent energetic polymer but until now a method of synthesis could not be found that would produce nearly difunctional material with acceptable hydroxyl equivalent weights. Nor has it been possible to formulate acceptable unplasticized "clean" PGN solid propellants having reduced levels of solids.

In copending application Ser. No. 07/561,797, filed on Aug. 2, 1990, assigned to the same Assignee as this Application, there is described a process for the production of atactic PGN that produces nearly difunctional material with acceptable hydroxyl equivalent weights, particularly PGN having a functionality of nearly 2.0 or more, or essentially equivalent to the hydroxy functionality of the polyol initiator employed in the process, and a hydroxyl equivalent weight of about 1000-1700 or more, preferably about 1200 to 1600. Moreover, that Application provides a process for producing atactic PGN by the polymerization of racemic glycidyl nitrate that has present greatly reduced amounts of cylic oligomer, that is about 2-5% by weight or less of said oligomer.

Improved atactic PGN produced according to the process of said copending Application has been found to permit the production of high energy solid propellants.

However, poly(glycidyl nitrate) produced according to the previously known processes as well as poly(glycidyl nitrate) produced according to the process of said copending Application have all produced PGN polymer with atactic stereochemistry. As a result, the PGN polymer is a highly viscous liquid which must be cured or cross-linked with di-and/or polyfunctional isocyanates to provide elastomeric binders for the solid propellants.

Conventional solid propellant binders which utilize cross-linked elastomers are those in which prepolymers are cross-linked by chemical curing agents. As outlined in detail in U.S. Pat. No. 4,361,526, there are important disadvantages to using cross-linked elastomers as binders. Cross-linked elastomers must be cast within a short period of time after addition of the curative, which time period is known as the "pot life". Disposal of a cast, cross-linked propellant composition is difficult, except by burning, which poses environmental problems. Furthermore, current state-of-the-art propellant compositions have serious problems that include, but are not limited to: use of non-energetic binders, high end-of-mix viscosities, thermally labile urethane linkages, and extreme vulnerability to unscheduled detonation.

In view of inherent disadvantages of cross-linked elastomeric polymers as binder materials, there has been considerable interest in developing thermoplastic elastomers suitable as binders for solid, high-energy compositions. However, many thermoplastic elastomers fail to meet various requirements for propellant formulations, particularly the requirement of being processable below about 120.C, it being desirable that a thermoplastic elastomeric polymer for use as a binder in a high-energy system have a melting temperature of between about 40° C. and about 120° C. The lower end of this range relates to the fact that the propellant composition may be subject to somewhat elevated temperatures during storage and use, and it is undesirable that significant softening of the propellant composition occur. The upper end of this range is determined by the instability, at elevated temperatures, of many components which ordinarily go into propellant compositions, particularly oxidizer particulates and energetic plasticizers.

It is therefore highly desirable to provide a PGN polymer which is a crystalline solid material suitable for use as a hard block of a PGN-based thermoplastic elastomer for use as a binder in solid propellants.

SUMMARY OF THE INVENTION

It has been discovered that isotactic PGN is a crystalline solid having a melting point of 47.2° C. ($\overline{M}n=2231$). Thus, this material is usable for the preparation of crystalline hard blocks for PGN-based thermoplastic elastomer solid propellant binders. Isotactic PGN is produced according to this invention by polymerizing chiral 2-(R)-glycidyl nitrate or its enantiomer, 2-(S)-glycidyl nitrate, according to the process described in the aforementioned copending application Ser. No. 07/561,797, filed on Aug. 2, 1990, for the preparation of PGN. Chiral 2-(R)-glycidyl nitrate for said polymerization can be prepared by sequential treatment of chiral (S) glycidyl tosylate with nitric acid and sodium hydroxide or by the direct nitration of commercially available 2-(S)-glycidol. Chiral (S) tosylate can be produced by Sharpless epoxidation of allyl alcohol or from the reaction of (R) glycidol with tosyl chloride and triethylamine. Isotactic PGN produced according to the present invention is usable as hard blocks for PGN-based thermoplastic elastomer solid propellant binders.

DETAILED DESCRIPTION OF THE INVENTION

Chiral (R) glycidyl nitrate for polymerization to isotactic optically active PGN can be produced from the known chiral (S) glycidyl tosylate or by direct nitration of (S) glycidol with acetyl nitrate or other nitrating agents. The chiral 2-(S)-glycidyl tosylate was converted into chiral 2-(R)-glycidyl nitrate by treatment first with nitric acid, e.g. 70% aqueous HNO₃, at about 10° C. or less under a nitrogen atmosphere, then by treatment with sodium hydroxide, e.g. 50% aqueous NaOH, at about 10° C. or less, followed by purification of the reaction product by fractional distillation to obtain the chiral 2-(R)-glycidyl nitrate as a colorless liquid. The reaction is illustrated by the following equation:

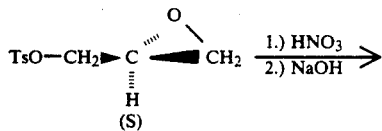

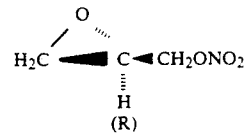

The 2-(R)-glycidyl nitrate (or its enantiomer) is then converted into isotactic PGN by the process described in the aforementioned copending application Ser. No. 07/561,797, filed on Aug. 2, 1990. In said copending Application, the process for the production of PGN, in which cylic oligomer formation is suppressed and PGN having a functionality substantially equal to the functionality of the polyol initiator and an acceptable hydroxyl equivalent weight is obtained, is provided by a process wherein a catalyst-initiator complex is formed and reacted with glycidyl nitrate (GN) and wherein the ratio of mols catalyst/mol hydroxyls in the initiator is <1:1, the glycidyl nitrate is added to the catalyst-initiator complex reaction mixture at a rate substantially equivalent to the rate at which it reacts with the complex such that no effective net amount of glycidyl nitrate monomer is built up, i.e. monomer is used up essentially as fast as it is added to the reaction mixture, and the reaction temperature is maintained within the range of from about 10°-25° C. Additionally, the process provides for the removal of any potential alkoxide groups, such as ethoxide groups, from the catalyst-initiator complex mixture when the catalyst employed in the process leads to the formation of such groups.

According to the process described in said copending Application glycidyl nitrate,

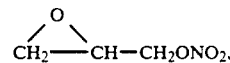

is polymerized to PGN,

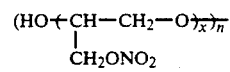

initiator, wherein n is an integer essentially equivalent to the hydroxy functionality of the initiator and x is an integer representing the repeating units, by forming a catalyst-initiator complex and reacting the complex with glycidyl nitrate and wherein the ratio of mols catalysts/mols hydroxyls in the initiator is <1:1, the glycidyl nitrate monomer is added to the catalyst-initiator complex reaction mixture at a rate in which the monomer is used up (reacted) essentially as fast as it is added, and the reaction temperature is maintained at a temperature within the range of from about 10° to 25° C.

The polymerization reaction is a cationic polymerization process conducted using a polyol initiator and an acid catalyst. The acid catalyst may be chosen from among those known in the art, including BF₃, HBF₄ and triethyloxonium hexafluorophosphate (TEOP). The Lewis acid catalyst forms a preinitiator complex with the polyol, for example, butanediol is known to form a complex with boron trifluoride (BF₃).

The polyol initiator employed generally has the hydroxyl groups of the polyol unhindered. The polyol is preferably a diol. As examples of suitable diols there may be mentioned ethylene glycol, propylene glycol, 1,3-propanediol and 1,4-butanediol. Suitable triols include, but are not limited to glycerol, trimethylolpropane and 1,2,4-butanetriol. A suitable tetrol is, but is not limited to 2,2,-(oxydimethylene)bis-(2-ethyl-1,3-propanediol). The molecular weight of the polyol is relatively low, preferably less than 500, more preferably below 300 and most preferably below about 150.

The acid catalyst is used at a much lower level relative to hydroxyl groups of the polyol than is taught in the prior art. It was discovered that a much more controlled reaction occurs if the catalyst, such as a Lewis Acid, is used at a molar ratio relative to hydroxyl groups of the polyol of less than 1:1, preferably from about 0.4:1 to about 0.8:1. If a proton acid is used as the catalyst, the ratio of hydrogen ions released by the acid catalyst to the hydroxyl groups of the alcohol is also less than 1:1, preferably 0.4:1 to about 0.8:1. By using a substantially lower level of acid catalyst, incorporation of a greater percentage of the polyol molecules internally within polymer molecules is achieved, cylic oligomer formation is suppressed to a level of about 2 to 5% or less, and lower polydispersity is achieved.

The cationic polymerization reaction may be carried out in a suitable organic solvent conducive to the cationic polymerization. If a solvent is employed, such suitable solvent is a non-protic, non-ether, inert solvent. Such solvents include, but are not limited to methylene chloride, chloroform, and 1,2-dichloroethane.

The polymerization reaction is conducted in a manner whereby the glycidyl nitrate monomer is added to the reaction mixture at a rate essentially equivalent to its rate of reaction, so that no effective net concentration of monomer is built up in the reaction mixture and the reaction temperature is maintained at a temperature within the range of from about 10° to 25° C., preferably from about 11° to 17° and most preferably about 13° to 15° C. It will be appreciated that the faster heat is taken away from the reactive mixture the faster glycidyl nitrate monomer can be added to the reaction mixture.

When the reaction of catalyst and initiator results in the formation of alkoxide groups in the catalyst-initiator complex, such as for example, the presence of alkoxide group compounds in the reaction mixture formed by the reaction of boron trifluoride etherate and 1,4-butanediol, the resulting PGN products are low in functionality. Pre-reacting the polyol 1,4-butanediol and boron trifluoride etherate and then removing diethylether under vacuum produces a PGN product essentially free of alkoxide groups. If, however, the catalyst and initiator would not form products containing such alkoxide groups, such as when boron trifluoride gas is employed instead of boron trifluoride etherate, then prereaction of the catalyst and initiator and removal of potential alkoxide compounds is not necessary.

The hydroxyl equivalent weight of the isotactic PGN polymer produced according to this process will generally be from about 1000 to 1700 or more, preferably from about 1200 to about 1600 and the amount of cyclic oligomer produced will generally be about 2-5% by weight or less.

Chiral 2-(S)-glycidyl tosylate or 2-(R)-glycidyl tosylate for producing chiral 2-(R)-glycidyl nitrate or 2-(S)-glycidyl nitrate, respectively, are known and can be produced, for example, from allyl alcohol by a Sharpless epoxidation or by the direct tosylation of commercially available chiral glycidol. Such an epoxidation reaction is described in Klunder, J. M., Soo, Y. K., Sharpless, K. B., *J. Org. Chem.*, 1986, 51, 3710-3712. The reaction is illustrated by the following equation in which the (S) tosylate is produced:

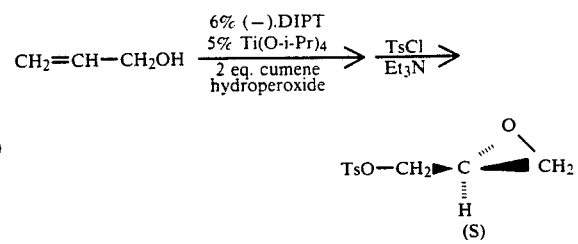

The isotactic PGN produced according to the invention is a crystalline solid having a melting point of 47.2° C. and can serve as the hard block of a PGN-based thermoplastic elastomer solid propellant binder. Such PGN-based thermoplastic solid propellants would offer numerous advantages over standard cured or crosslinked propellant elastomers, such as for example, they could be extruded, would be easily recast, could be removed from a rocket motor case without potentially dangerous operations and would not be subject to pot-life restrictions.

The invention is exemplified in the following illustrative example.

Preparation of 2-(S)-Glycidyl Tosylate

Following a procedure of the aforementioned Klunder et al. article, a solution of D (−) diisopropyl tartrate (14.0 g, 0.06 mol, dried over 3 Å molecular sieves) in anhydrous dichloromethane (15 mL) was added via a cannula to an oven dried, 5-L-4-neck-round bottom flask (equipped with a thermometer, nitrogen inlet, a mechanical stirrer, and rubber septum) containing a stirred mixture of anhydrous dichloromethane (1.9 L) and activated 3 Å ground molecular sieves under $N_2$. Additional dichloromethane (10 mL) was used to rinse residual tartrate into the reaction flask. Allyl alcohol (58.1 g, 1.0 mol, dried over 3 Å molecular sieves) was added and the reaction mixture was cooled to −5° C. under a positive $N_2$ flow. Dry titanium isopropoxide, (Ti—O—i—Pr)$_4$, (15.0 mL, 14.3 g, 0.5 mol) was then added by syringe and the mixture was allowed to stir for 30 min. Cumene hydroperoxide (363.7 g, 1.91 mol, 80%, precooled to 1° C.) was added dropwise, via a cannula to the reaction mixture over 1 h, while maintaining an internal reaction temperature of <2° C. After the peroxide addition was compete, the reaction mixture was allowed to stir under $N_2$ at −5 to 0° C. for 6 h. The mixture Was then cooled to −20° C., and trimethylphosphite (164.9 g, 1.29 mol, 97%, dried over molecular sieves) was added slowly, via a cannula over 1.2 h, while not allowing the reaction temperature to exceed −10° C. The amount of phosphite added for the peroxide reduction was determined by TLC (40% EtOAc/hexane; tetramethylenediamine spray indicator (1.5 g in 128:25:1 mL, MeOH: $H_2O$: AcOH). After the very exothermic phosphite addition was complete, dry triethylamine (128.3 g, 1.26 mol, 99%) was added in one portion, followed by the addition of a solution of p-toluenesulfonylchloride (204.5 g, 10.05 mol, 98%) in dry dichloromethane (250 mL). After initially being stirred for 15 min, the reaction mixture was allowed to stand for 12 h at −20° C. under $N_2$. The mixture was then allowed to warm to room temperature and filtered through celite (about 65 g). The celite pad was rinsed with additional dichloromethane (200 mL) and the combined filtrate washed with 10% aqueous tartaric acid (2×150 mL), then brine (300 mL), and was dried over anhydrous MgSO$_4$, and was filtered. The solvent was then evaporated (65° C., 0.3 mm) to give an amber oil (333.7 g). The crude oil was filtered through a column of silica gel (286 g) eluting with dichloromethane. The combined filtrates were evaporated in vacuo affording a light amber oil (307.1 g). In order to obtain seed crystals, a portion of the crude oil (26.7 g) was subjected to column chromatography (silica gel; EtOAc: hexanes, 1:1) to give crude tosylate (12.2 g) as a light yellow oil. This oil was recrystallized (2 ×) from a minimum quantity of warm Et$_2$O: hexane (6:1) solution to give 2-(S)-glycidyl tosylate (9.5 g) as colorless crystals; DSC (mp 44.8° C., exotherm 277.3° C., 37 J/g); [α] $D^{25}$ = +15.59 (c2.13, CHCl$_3$); 83.7% ee. IR (KBr) 3077, 3002, 2937, 1599, 1361, 1178, 963, 828, 668 cm$^{-1}$. $^1$H-NMR (400 MHz, CDCl$_3$) δ7.81 (d, J=8 Hz, 2H), 7.36 (d, J=8 Hz, 2H), 4.26 (dd, J$^3$=3, 11 Hz, 1H), 3.96 (dd, J=6, 11 Hz, 1H), 3.16–3.23 (m, 1H), 2.82 (t, J=5 Hz, 1H), 2.60 (dd, J=3, 5 Hz, 1H), 2.46 (s, 3H). These crystals were used to seed the remaining oil (280.4 g) which was dissolved in a minimum quantity of Et$_2$O: hexanes (6:1) and recrystallized twice to afford a total amount of glycidyl tosylate (89.1 g, 39%) as colorless crystals. DSC, IR, and $^1$H-NMR data for the total amount of tosylate was identical in all essential respects to the data listed above. The average specific rotation was as follows: [α] $D^{25}$ = +15.96 (c2.13, CHCl$_3$); 85.7% ee$^2$.

Preparation of 2-(R)-Glycidyl Nitrate from 2-(S)-Glycidyl Tosylate

Solid 2-(S)-glycidyl tosylate (67.0 g, 0.294 mol [α] $D^{25}$ = +15.85 (c2.13, CHCl$_3$), 85% ee) was slowly added over 1.2 h, via a solid addition funnel, to a rapidly stirred solution of 70% aqueous HNO$_3$ (28.0 g, 0.311 mol) at −15° C. under N$_2$. The glycidyl tosylate addition rate was controlled so as to maintain a reaction temperature of ≦10° C. After the addition was complete, the mixture was allowed to stir for 2.5 h at 10° C. under N$_2$. The reaction mixture was then cooled to −10° C. and 50% aqueous NaOH (32.3 g, 0.404 mol) was added dropwise over 0.75 h at a rate so as not to exceed a reaction temperature of 10° C. Distilled H$_2$O (59 mL) was added to dissolve a solid precipitate and the resultant solution was allowed to stir for 30 min, while the reaction temperature was allowed to rise to about 25° C. Additional distilled H$_2$O (31 mL) was then added and the reaction solution extracted with dichloromethane (2×280 mL+1×100 mL). The combined dichloromethane extract was dried over anhydrous Na$_2$SO$_4$, was filtered, and was stored in a freezer for 12 h. The solvent was then evaporated in vacuo to give a yellow oil (30.6 g; 88%). This material was purified by fractional distillation (pot temp.=45° C., head temp.=27°–28° C., P=0.370 mm) to afford 2-(R)-glycidyl nitrate (GN) as a colorless liquid. Weights and purities (GC, Porapak Q, 1.5ft, 140° C., flow rate =100 mL/min) of the fractions were as follows: F-1 (2.4 g, 85%); F-2 (5.3 g, 91%); F-3 (13.1 g, 95%); F-4 (9.3 g, 97%); F-5 (9.6 g, 97%); F-6 (2.5 g, 97%). Fractions 4, 5, and 6 were used to prepare isotactic PGN and had the following specific rotations [α] $D^{25}$=(2.13, CHCl$_3$); F-4 (−29.65°); F-5 (−28.18°); and F-6 (−30.01°). Portions of these fractions were then combined to produce 12.27 g of glycidyl nitrate (avg. [α] $D^{25}$=28.61°; 2.13, CHCl$_3$) to be polymerized. An analytical sample of glycidyl nitrate was obtained by repeated fractional distillation (GC purity 98%). [α] $D^{25}$ = −27.36° (c2.15, CHCl$_3$). DSC (endotherm 143.5° C., 252 J/S) IR (NaCl) 3071 (w), 3009–2905 (w), 1642 (s), 1427 (m), 1360 (m), 1285 (s), 866 (s), 758 (m) cm$^{-1}$. $^1$H-NMR (400 MHz, CHCl$_3$) 4.78 (dd, J=2.6, 12.6 Hz, 1H), 4.33 (md, 1H), 3.27 (m, 1H), 2.90 (m, 1H), 2.71 (m, 1H).

Preparation of 2-(R)-Glycidyl Nitrate from 2-(S)-Glycidol

Nitric acid (31.9 g, 0.51 mol, 100%) was added dropwise to acetic anhydride (47.8 mL, 0.51 mol, Fisher) at 15° C. under N$_2$. The nitric acid addition rate was controlled so as not to exceed a reaction temperature of 20° C. The acetyl nitrate solution was allowed to stir for 30 min at 15° C. and was then added dropwise to a solution of 2-(S)-Glycidol (25.8 g, 0.34 mmol, ARCO, 86% purity, 86% ee, [α] (neat)= −14°) in CH$_2$Cl$_2$ (70 mL) cooled to −10° C. under N$_2$. The acetyl nitrate addition rate was controlled so as not to exceed a reaction temperature of −5° C. After the addition was complete, the reaction mixture was allowed to stir for 2.5 h. at 4°–5° C. and was quenched with ice H$_2$O (250 mL). The mixture was extracted with CH$_2$Cl$_2$ (3×75 mL). The combined CH$_2$Cl$_2$ extract was washed with saturated aqueous NaHCO$_3$ (3×50 mL), was dried over anhydrous MgSO$_4$, and was filtered. Evaporation of the filtrate provided a yellow liquid (47.2 g). GC analysis (Porasil Q) of the crude product indicated that the volatile components consisted of glycidyl nitrate (GN, 68.7%), glycidol (Gly, 5.2%), and acetic anhydride (Ac$_2$O, 26.1%). Fractional distillation (28° C., 0.37 mm) of the mixture provided purified fractions of chiral GN. Further purification of GN fractions by column chromatography (silica gel, ethyl acetate: hexanes, 1:2) provided a purified sample of 2-(R)-glycidyl nitrate. [α] $D^{25}$ = −28.56° (2.13, CHCl$_3$). G.C. (mole %) 96.1% GN; 2.6% Gly, 1.3% Ac$_2$O. The IR and $^1$H-NMR spectra of this material were identical in all essential respects with those of an authentic sample of 2-(R)-glycidyl nitrate prepared from 2-(S)-glycidyl tosylate.

Preparation of Isotactic Poly(glycidyl nitrate)

Boron trifluoride etherate (0.58 mL, 0.67 g, 0.005 mol) was added, via syringe, to rapidly stirred 1,4-butanediol (0.42 mL, 0.42 g, 0.005 mol) under N$_2$. The BF$_3$.OEt$_2$ addition was maintained so as not to exceed a reaction temperature of 23° C. After the addition was complete, the solution was allowed to stir for 1 h and the ether was removed under high vacuum (1 h). The resulting pink viscous residue was then dissolved in anhydrous CH$_2$Cl$_2$ (8.2 mL) and this solution was cooled to 11° C. A solution of chiral glycidyl nitrate (12.27 g, 0.10 mol, 97% purity, avg. [α] $D^{25}$= −28.61°) in anhydrous CH$_2$Cl$_2$ (11 mL) was then added dropwise to the butanediol-BF$_3$/CH$_2$Cl$_2$ solution at a rate so as to maintain a reaction temperature of 13°±2° C. The reaction became exothermic reaching a temperature of 42° C. after about 70% of the GN solution had been added. After the addition was complete (40 min total addition time), the progress of the reaction was monitored by $^1$H-NMR (60 MHz, CHCl$_3$). The disappearance of the signals due to GN (i.e. δ3.27, 2.90, and 2.71) and the appearance of signals due to PGN (at δ4.60 and 3.80 indicated the reaction was complete. The mixture was then quenched with brine (5 mL) and was washed with saturated aqueous NaHCO$_3$ (3×5 mL). The organic fraction was then dried over anhydrous MgSO$_4$, was filtered, and the CH$_2$Cl$_2$ was evaporated in vacuo to afford crude PGN (12.18 g, 99%) as a viscous yellow oil which solidified upon standing at 25° C. in ca. 3 days. GPC (THF, P=1500 psi) of this material indicated a bimodal polymeric distribution ($\overline{M}w=1125$; $\overline{M}n=1485$) with a polydispersity of 1.32 (calculated M.Wt=2626). This material was triturated with methanol (100 mL) and allowed to sit under this solvent for about 4 h. The supernatent was then decanted and the solvent evaporated in vacuo to give fraction 1 (3.44 g), as a tacky, light-colored viscous oil. The methanol insoluble residue was triturated again with methanol (100 mL), and the mixture was allowed to stand 4 h, and the supernatent decanted. Evaporation of the solvent gave fraction 2 (2.80 g) as a light yellow viscous oil. This process was repeated again to afford fraction 3 (1.25 g), which was also a light yellow viscous oil, and a crystalline methanol-insoluble polymer (4.49 g). GPC indicated fractions 1, 2, and 3 had bimodal polymeric distributions and showed the following specific rotations ($[\alpha]$ $D^{25}$, CHCl$_3$) and $\overline{M}n$ and $\overline{M}w$, respectively: #1 (−29.0°, 992, 1215), #2 (−25.9°, 1067, 1325) and #3 (−22.8°, 1335, 1649). The crystalline isotactic polymer had an $[\alpha]$ $D^{25}=-29.7°$ (CHCl$_3$) and was homogeneous by GPC ($\overline{M}n=2231$; $\overline{M}w=2644$; $\overline{M}w/\overline{M}n=1.19$). DSC (mp 47.2° C.; exotherm 210.9° C.; 200 J/g). IR (NaCl) 2896 (m), 1631 (s), 1462 (w), 1282 (s), 1141 (m), 988 (m), 857 (s) cm$^{-1}$. $^1$H-NMR (400 MHz, CHCl$_3$) δ4.76–4.62 (m, 1.5 relative H area), 4.62–4.20 (m, 14), 4.05–3.90 (m, 1), 3.90–3.20 (m, 23.5), 1.70–1.30 (m, 1.75).

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. Isotactic poly(glycidyl nitrate)

2. A process for the preparation of isotactic poly(glycidyl nitrate) by cationic polymerization of chiral (R) glycidyl nitrate or the (S) enantiomer thereof in the presence of a polyol initiator and an acid catalyst, said process comprising forming a catalyst-initiator complex and reacting said complex with chiral (R) glycidyl nitrate or the (S) enantiomer thereof to produce isotactic poly(glycidyl nitrate) and wherein the ratio of mols catalyst/mol hydroxyls in the initiator is <1:1, the chiral (R) glycidyl nitrate or the (S) enantiomer thereof is added to the catalyst-initiator complex at a rate substantially equivalent to the rate at which the chiral (R) glycidyl nitrate or the (S) enantiomer thereof reacts with the complex such that no effective net amount of chiral glycidyl nitrate monomer is built up, and the reaction temperature is maintained within the range of from about 10°–25° C.

3. A process according to claim 2 wherein the polyol initiator is butanediol.

4. A process according to claim 3 wherein the catalyst is BF$_3$, HBF$_4$, BF$_3$.etherate, or HBF$_4$.etherate.

5. A process according to claim 4 wherein the ratio of mols catalyst/mols hydroxyl groups of the initiator is from about 0.4:1 to about 0.8:1.

6. A process according to claim 2 wherein the reaction temperature is maintained at a temperature within the range of from about 11° to about 17° C.

7. A process according to claim 2 in which oligomer formation is suppressed and the isotactic poly(glycidyl nitrate) produced has a functionality substantially equal to the hydroxy functionality of the polyol initiator employed.

8. A process according to claim 6 in which oligomer formation is suppressed and the isotactic poly(glycidyl nitrate) produced has a functionality substantially equal to the hydroxy functionality of the polyol initiator employed.

* * * * *